(12) United States Patent
Odungattu Thodiyil et al.

(10) Patent No.: US 12,036,072 B2
(45) Date of Patent: Jul. 16, 2024

(54) ULTRASOUND IMAGING APPARATUS AND METHOD

(71) Applicant: KONINKLIJKE PHILIPS N.V., Eindhoven (NL)

(72) Inventors: Anumod Odungattu Thodiyil, Bangalore (IN); Srikanth Shettigar, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 369 days.

(21) Appl. No.: 16/963,869

(22) PCT Filed: Jan. 9, 2019

(86) PCT No.: PCT/EP2019/050357
§ 371 (c)(1),
(2) Date: Jul. 22, 2020

(87) PCT Pub. No.: WO2019/145141
PCT Pub. Date: Aug. 1, 2019

(65) Prior Publication Data
US 2021/0038192 A1    Feb. 11, 2021

(30) Foreign Application Priority Data

Jan. 23, 2018 (EP) ..................... 18152998

(51) Int. Cl.
*A61B 8/00* (2006.01)
*A61B 8/08* (2006.01)

(52) U.S. Cl.
CPC .......... *A61B 8/4477* (2013.01); *A61B 8/0841* (2013.01); *A61B 8/4472* (2013.01);
(Continued)

(58) Field of Classification Search
CPC ... A61B 8/4477; A61B 8/0841; A61B 8/4472; A61B 8/466; A61B 8/5207; A61B 8/54; A61B 8/5253; A61B 8/14
See application file for complete search history.

(56) References Cited

U.S. PATENT DOCUMENTS 11,134,858 B1 * 10/2021 Owsley ................ A61B 5/7257
2006/0173338 A1 * 8/2006 Ma .......................... A61B 8/462
600/456
(Continued)

FOREIGN PATENT DOCUMENTS

| JP | S5578948 A | 6/1980 |
| JP | 2010094361 A | 4/2010 |
| WO | 2016198413 A1 | 12/2016 |

OTHER PUBLICATIONS

International Search Report and Written Opinion for International Application No. PCT/EP2019/050357, filed Jan. 9, 2019, 12 pages.

*Primary Examiner* — Boniface N Nganga

(57) ABSTRACT

Ultrasound imaging apparatus for imaging a region of interest in a subject comprises a plurality of separate ultrasonic probes (2a-2c) each having at least one transducer (72) for transmitting and receiving ultrasonic waves and a communications unit. A control unit (1) controls the probes to coordinate their operation in sequence, and obtains ultrasonic images from the probes for generating a display of those images together in real time simultaneously. The control unit transmits control signals to at least one of the probes, and each probe receives control signals from the control unit and/or from an adjacent one of the probes. The control signals cause the probes to execute a scan sequentially in a predetermined probe sequence which is usually repeated, and the control unit generates a display by combining the image data from the probes.

14 Claims, 6 Drawing Sheets

(52) U.S. Cl.
CPC ............ *A61B 8/466* (2013.01); *A61B 8/5207* (2013.01); *A61B 8/54* (2013.01)

(56) References Cited

U.S. PATENT DOCUMENTS

| | | | |
|---|---|---|---|
| 2008/0052028 A1* | 2/2008 | Pickerd | G01R 35/005 |
| | | | 702/109 |
| 2010/0268503 A1 | 10/2010 | Specht et al. | |
| 2011/0061466 A1 | 3/2011 | Nishino | |
| 2012/0179037 A1 | 7/2012 | Halmann | |
| 2014/0046188 A1 | 2/2014 | Yen et al. | |
| 2014/0058261 A1 | 2/2014 | Chioka et al. | |
| 2014/0343429 A1* | 11/2014 | Jensen | A61B 8/56 |
| | | | 600/443 |
| 2015/0032002 A1* | 1/2015 | Rothberg | A61B 8/4483 |
| | | | 600/440 |
| 2015/0382208 A1* | 12/2015 | Elliott | H04W 24/02 |
| | | | 370/252 |
| 2016/0030003 A1* | 2/2016 | Liu | A61B 8/54 |
| | | | 600/440 |
| 2016/0089108 A1 | 3/2016 | Kim | |
| 2016/0089117 A1* | 3/2016 | Kim | A61B 8/14 |
| | | | 600/443 |
| 2016/0345933 A1* | 12/2016 | Bartlett | G01S 7/52079 |
| 2017/0168148 A1* | 6/2017 | Radulescu | G01S 15/8993 |
| 2021/0298719 A1* | 9/2021 | Elevelt | A61B 8/085 |
| 2021/0302322 A1* | 9/2021 | Tsai | G01J 3/2823 |

* cited by examiner

ULTRASOUND IMAGING APPARATUS AND METHOD

RELATED APPLICATIONS

This application is the U.S. National Phase application under 35 U.S.C. § 371 of International Application No. PCT/EP2019/050357, filed on Jan. 9, 2019, which claims priority to European Application No. 18152998.3, filed Jan. 23, 2018. These applications are hereby incorporated by reference herein.

FIELD OF THE INVENTION

This invention relates to ultrasound imaging, especially medical imaging of the human body.

BACKGROUND OF THE INVENTION

Currently most medical ultrasound machines use a single transducer, also referred to as a probe, for patient diagnosis. The transducer transmits ultrasound waves and captures the reflected echo, typically using an array of piezoelectric elements. The echoes are subsequently converted to images for the final rendering to generate display data. The reflected echo intensity depends upon the echogenicity of the scanned tissue, organs or any structure in the region of interest. Depending upon the echogenicity, the structure could be hyperechoic (white on the display screen), hypoechoic (grey on the screen) or anechoic (black on the screen). Most of the time using a single ultrasound transducer it is difficult to see tissues or organs underlying an anechoic structure such as bone, so a lot of clinically relevant information remains hidden. This is known as the acoustic shadowing artefact. Also due to the echogenicity of different organs, tissues and external structure, various other types of imaging artefact can occur. These imaging artefacts are echoes that are parts of the image that do not have a true mapping to the region of interest like other tissue, or needle structures when invasive surgery is being imaged. While viewing an ultrasound image, the user has to be aware of the possible occurrence of these artefacts, and a knowledge of the different kinds of artefacts is necessary to avoid false diagnosis.

In addition to these artefacts, a so-called reverberation artefact can be caused by ultrasound beams reverberating between parallel reflectors before reaching the probe. The ultrasound signals returning after these reverberations are incorrectly viewed as being returned from deeper structures, since it took them longer to return to the probe. This artefact can be reduced by carefully changing the angle of probe placement so that reverberation between strong parallel reflectors cannot occur.

Using a single probe for scanning the patient, it is not easy to differentiate between normal tissue and artefacts when looking at the echo images. Images of the same regions need to be recaptured and reviewed after moving or changing the angle of the probe.

Another problem found during diagnosis using a single probe is in the scanning of large organs such as the lung, placenta and kidney, and organs having motion such as the heart and the foetus. Due to the limited Field of View (FoV) of a single probe, the sonographer needs to move the probe to get a better understanding of the organ. It is better to have a larger FoV in such diagnosis.

The problems of image obstruction and image quality were recognised in WO2016/198413, which discusses multi-probe arrays under development especially for use in large area transthoracic echocardiography, LATTE. The probes are arranged in fixed relation to one another, and the images they receive are combined to form an overview image, or are displayed separately so as to show different parts of the same organ from different viewing directions. The ultrasound imaging apparatus disclosed in WO2016/198413 was aimed at overcoming the disadvantage of displaying those images with different image qualities arising from the orientations of the imaged structures, and avoiding the need for cumbersome manual optimization of the imaging. The apparatus had an array of probes, and a processor that determined the spatial relationship of each probe with the anatomical object being imaged by the array, by computerized segmentation of the shape of the surface of the object, and that selected one or more of the images from the probes based on the image quality as affected by the spatial relationship. For Doppler imaging of blood flow, the probe whose axis was closest to the normal to the surface being viewed could be selected automatically for providing the image.

US 2016/0030003A discloses the use of probes positioned on different parts of the patient to provide real-time "synchronous" scanning of the different body parts and displaying them all at the same time. This is achieved by controlling the probes according to a preset sequence, for example temporally interleaving the scan lines of the different probes, to acquire the respective image frames in parallel, or else obtaining whole image frames from the different probes sequentially.

US 2014/343429 A1 discloses an ultrasound imaging system that comprises a beamformer configured to beamform ultrasound signals. The beamformer includes input/output configured to at least receive ultrasound signals, first and second ultrasound probe connectors and a switch that concurrently routes ultrasound signals concurrently received via the first and second ultrasound probe connectors to the beamformer, which processes the ultrasound signals.

There remains a need for a system capable of imaging large organs, or organs having motion, from different angles at the same time over a large field of view, so as to view the same organ from different perspectives, thus improving the image quality while isolating the artefacts.

SUMMARY OF THE INVENTION

The invention is defined by the claims.

According to an aspect of the invention, there is provided ultrasound imaging apparatus for imaging a region of interest in a subject, comprising:
  a control unit;
  a plurality of separate ultrasonic probes coupled to the control unit, each probe comprising:
    at least one transducer for transmitting and receiving ultrasonic waves;
    a receiver for receiving a probe scan signal for triggering an ultrasound scan by the probe; and
    an output for providing an ultrasound image;
  wherein the control unit is adapted to:
    control the probes to coordinate their operation in a predetermined probe sequence by providing a probe scan signal to at least one of the probes; and
    receive ultrasonic images from the outputs of the probes, for the generation of a combined display of the images from the probes;

and wherein the apparatus is configured to coordinate the operation of the probes in the predetermined probe sequence either:

by each probe transmitting a scan state signal indicative of its own scan being completed, for reception by the next probe as the probe scan signal, or by the control unit for sending the next probe a probe scan signal; or by each probe storing a local clock synchronized to a global clock common to the probes, and responding to the probe scan signal from the control unit to execute its own scan at a scan timing based on its local clock.

Preferably, the scan sequence is repeated. This enables image frames to be accumulated from successive line scans, and also enables viewing of the region of interest for substantial periods of time, for diagnosis or surgery.

The scanning and the collection of the image data is preferably done in real time, i.e. without any delay caused by storage of the data offline before its rendering or display. The image data from the probes is acquired by the control unit and may be combined and rendered by the same unit or by an external apparatus. The rendered images may be displayed by the same unit or by an external display.

It will be understood that a significant feature of the invention is that the probes themselves contribute to their sequencing, to avoid mutual collision. This is done either by their having local clocks set by a common global clock, or by their recording and transmission of their own scan state.

This apparatus is capable of imaging large organs, or organs having motion, from different angles at the same time over a large field of view, so as to view the same organ from different perspectives, thus improving the image quality and/or enlarging the field of view while isolating the artefacts. The probe sequencing avoids interference between the waves of the different probes.

In embodiments using an asynchronous protocol, the control unit comprises a global clock and each probe comprises a local clock and a memory storing a predetermined set of beamforming parameters for its transmission and reception of the ultrasonic waves in accordance with the local time determined by its local clock; the control unit being configured periodically to set or reset the local clocks by transmitting a clock signal to the communications unit of each respective probe from its communications unit; the beamforming parameters comprising sequencing information including the local time at which each probe is to start and end transmission and reception, to ensure the sequential operation of the probes so as to avoid mutual interference between their ultrasonic waves.

In embodiments using a synchronous protocol, each probe comprises a memory configured to store its own scan state representing the stage of progress of its own scan, the apparatus being configured to transmit the control signals between the control unit and the probes to control the probes to switch sequentially between scan states, whereby only one of the probes, which is the next in the predetermined probe sequence, commences a scan in response to information, contained in the control signal it receives, that the scan state of another probe, the current probe in the sequence, represents the completion of its scan.

In these synchronous embodiments, the control unit may directly control the probe sequencing. The memory of the control unit is then configured to store the scan state representing the stage of progress of the scan of each probe, and the control unit is configured to transmit and receive control signals to and from each probe, to instruct the first probe in the predetermined probe sequence to start its scan and then to instruct each next probe in that probe sequence to start its scan only once it has received from the previous probe in the sequence the information that it has completed its scan.

Alternatively, the memory of the control unit is configured to store the predetermined probe sequence, and to transmit a control signal to the first probe in the sequence to instruct it to start its scan; and each probe is configured, when it has completed its scan, to transmit a control signal to another of the probes, which is the next in the predetermined probe sequence, to instruct that other probe to start its scan. In this way, the probe-to-probe communications control the probe sequencing.

In any of these embodiments, the control unit memory may be configured to store probe position data representing the position of each probe, and the processor may be configured to combine the image data based on the relative positions of the probes. Each probe may comprise means for tracking its own position and storing corresponding position data in its memory.

Conveniently, each probe comprises an internal electric power source and its communications unit is configured for wireless communication with the control unit and/or the other probes.

The processor may be configured to combine the sequential real-time images from two of the probes that are separated by an inter-pupillary distance, to generate the display as a stereoscopic display for left eye and right eye projections.

From another aspect, the invention provides a method of ultrasound imaging a region of interest in a subject, using a plurality of separate ultrasonic probes disposed at different positions on the subject to view the same region of interest, the plurality of separate ultrasonic probes being coupled to a control unit, each probe comprising a receiver for receiving a probe scan signal for triggering an ultrasound scan by the probe, wherein the control unit is adapted to control the probes to coordinate their operation in the predetermined probe sequence by providing a probe scan signal to at least one of the probes, the method comprising causing the probes to execute respective scans, each scan comprising transmitting an ultrasonic beam to the region of interest and receiving reflections, the probes executing their scans sequentially in a predetermined probe sequence, which is preferably repeated, and combining the image data from the probes for display of the corresponding images together, preferably simultaneously or substantially simultaneously;

wherein the operation of the probes in the predetermined probe sequence is coordinated either:

by each probe transmitting a scan state signal indicative of its own scan being completed, for reception by the next probe as the probe scan signal, or by the control unit for sending the next probe a probe scan signal; or by each probe storing a local clock synchronized to a global clock common to the probes, and responding to the probe scan signal from the control unit to execute its own scan at a scan timing based on its local clock.

Each probe may comprise a local clock and a memory storing a predetermined set of beamforming parameters for its transmission and reception of the ultrasonic waves in accordance with the local time determined by its local clock; the method comprising periodically setting or resetting the local clocks from a global clock, and the beamforming parameters comprising sequencing information including the local time at which each probe is to start and end transmission and reception, to ensure the sequential execution of the scans by the probes, so as to avoid mutual interference between their ultrasonic waves.

Alternatively, without the need for clocking the probes, each probe stores its own scan state representing the stage of progress of its own scan, each probe executing its respective scan by switching between scan states, whereby only one of the probes, which is the next in the predetermined probe sequence, commences a scan in response to information it receives that the current probe in the sequence has completed its scan.

The method then preferably comprises either (a) storing centrally the scan state representing the stage of progress of the scan of each probe, and using this stored information to instruct the first probe in the predetermined probe sequence to start its scan and then to instruct each next probe in the probe sequence to start its scan only once the previous probe in the sequence has completed its scan; or (b) instructing the first probe in the predetermined probe sequence to start its scan; then each probe, when it has completed its scan, instructing the next probe in the predetermined probe sequence to start its scan.

Each probe may track its own position and the image data may be combined based on the relative positions of the probes. This provides a useful combination of images for the sonographer, for example by stitching together images of regions of a large organ from adjacent viewpoints, or fusing the images of the same region taken from different viewpoints and angles in order to optimize the quality of the combined image.

A further aspect of the invention is a computer program comprising computer program code means which is adapted, when said program is run on a computer of an ultrasonic imaging system, to implement the method described above.

BRIEF DESCRIPTION OF THE DRAWINGS

Particular embodiments of the invention will now be described in detail, by way of example only, with reference to the accompanying drawings, in which.

DETAILED DESCRIPTION OF THE EMBODIMENTS

Figure 1:
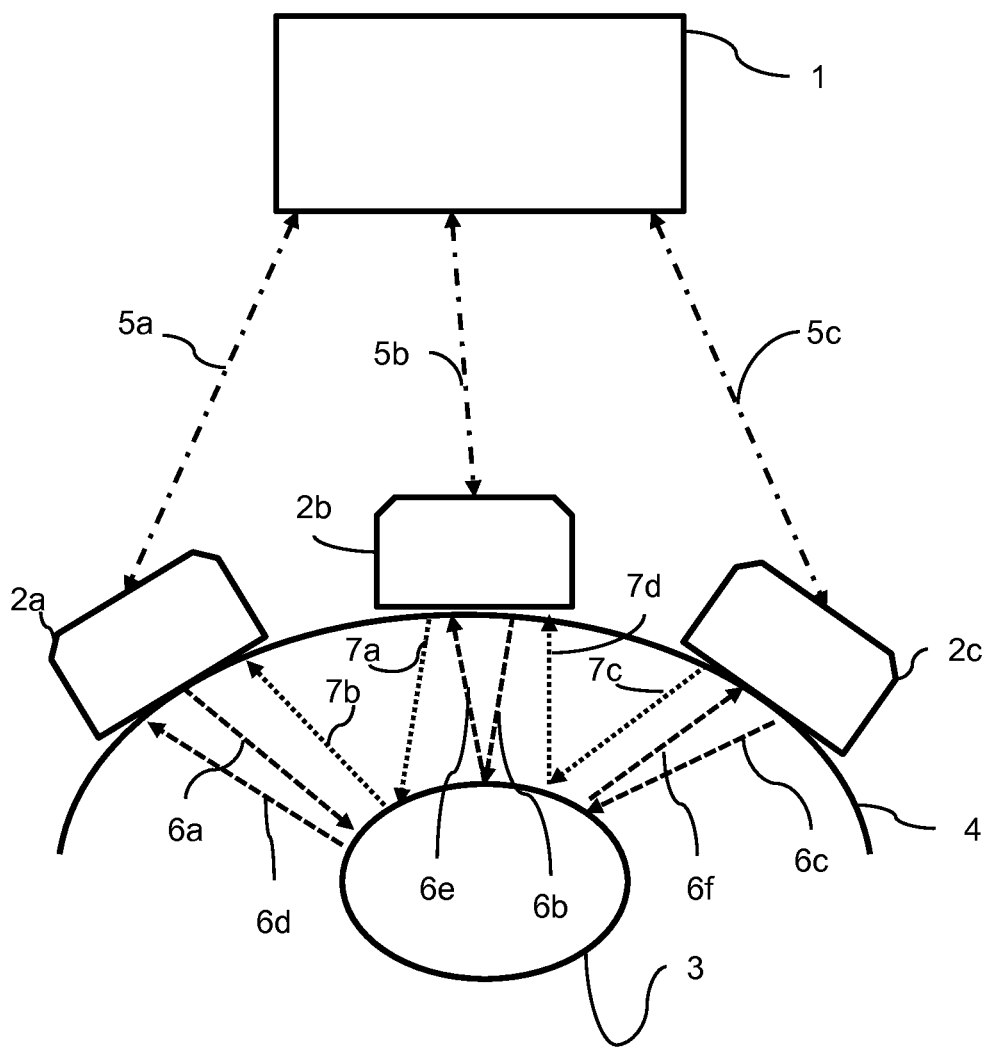
FIG. 1 illustrates the concept of a multi-probe ultrasound system in accordance with the invention.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The preferred embodiments provide an ultrasound imaging system for imaging a region of interest in a patient, comprising: a plurality of separate ultrasonic probes, preferably self-contained and portable and with their own rechargeable power supplies, each having at least one transducer for transmitting and receiving ultrasonic waves, and a communications unit. Each probe preferably has a fixed array of ultrasound transducers, and a controller for beam-forming e.g. to focus the ultrasound waves that are transmitted and/or those that are received. The system has an overall control unit comprising a processor and a memory, for controlling the probes to coordinate their operation in sequence, obtaining ultrasonic images from the probes and preferably rendering image data for a display of those images together, preferably in real time simultaneously or substantially simultaneously, and a communications unit. The control unit is configured to transmit control signals from its communications unit to at least one of the probes, and each probe is configured to receive control signals in its communications unit from the control unit and/or from an adjacent one of the probes. In this way, the control signals cause each probe to execute a scan, each scan comprising transmitting an ultrasonic beam to the region of interest and receiving reflections of that transmitted beam, and to transmit to the control unit in real time image data representing the received reflections. The control signals cause the probes to execute their scans sequentially in a predetermined probe sequence which is preferably repeated, and the control unit is configured to acquire the image data for the generation of the display together of the images from the probes.

This can avoid or mitigate the problems with existing single probe systems. Artefacts can be avoided by arranging the probes at different positions and/or at different angles on the patient so that the sonographer can select the best image, from one or more of the probes, for viewing. The field of view can also be extended by combining images from two or more of the probes, so as to image a large organ. Two adjacent probes can also be used to provide a stereoscopic display of the field of view, giving the sonographer depth information. The images can be 2D or 3D from each probe, using known techniques for beam-forming and image processing.

The combination of images of the same region of interest from different probes having different viewpoints is known in the art. To obtain a single final image from the image data sets acquired at each viewpoint, a process of image registration is performed. Registration consists in aligning the image data acquired in each data set such that the common visual features captured in each are rendered in alignment with one another (e.g. such that they overlap with one another). The two can then be combined or fused.

The registration or fusion of two real-time 3D ultrasound volumes (also known as 4D volumes or 4D image data sets) is a key step in multi-perspective echography, allowing the imaged field of view to be extended, and for missing information in one captured image data set to be supplemented by the information captured in the other. Moreover, fused echography provides for improved image quality and surgical device visibility.

Known methods for achieving registration of 4D ultrasound volumes typically make use of an optimization process based on combined similarity scores of intensity-normalized 2D images from selected 2D slices of the volumes to obtain the correct alignment of the 4D volumes.

This optimization process may further use representations of each 4D volume at different levels of detail (as represented in a so-called scale space) in order to increase the chances of converging to a meaningful solution. US 2006/0002632 discloses image registration by generating mesh nodes in an image at different mesh resolution level, generating a motion vector for each mesh node and matching it to a second image. Local motion vectors are determined by interpolation.

Instead of fusing the images from different viewpoints, 2D images obtained at nearly the same instant may be "stitched" together laterally, to provide a larger 2D image, e.g. of a large organ. This can avoid the need to move a probe. Stitching of images is also known in the art—it may include an automatic matching or correlation process in which the patterns of pixels along the adjacent edges of the images are compared in order to align the edges in 2D space. The key-points or features from two more images are detected from the lateral (overlapping) edges and feature detection algorithms are used to detect features like harris corners, blobs etc. Alignment may include magnification, warping and/or rotation, using known image processing techniques. Finally, on the stitched image the gray level intensity differences especially in the overlapping edges are averaged or adjusted to remove the stitching seam.

Some of the above steps are referenced in the patent US 20100014780.

FIG. 1 shows multi-probe usage in an ultrasound system. A control unit 1 is connected by wire or wirelessly to each of probes 2a, 2b and 2c as shown by lines 5a to 5c respectively. The probes are self-contained portable ultrasound probes that are positioned by a sonographer to image a region of interest, ROI 3 of a patient 4. The probes form ultrasound beams 6a, 6b, 6c that are transmitted to the region of interest 3 which partially reflects them as echoes 6d, 6e and 6f, providing image information from the field of view including the region of interest 3. This is normally B-mode ultrasound imaging, although other types of imaging are possible—for example, Doppler imaging could be interleaved with the B-mode imaging, in order to show movement for example of blood in an artery. The different types of image could be displayed together, as is known in the art.

The ultrasound system control unit 1 acts as a master to control the probes 2a, 2b and 2c as slaves. The system may contain multiple ultrasound system control units similar to control unit 1, all of which can communicate with all or a subset of the probes. The control unit 1 sends triggering sequence and timing information to the probes to fire ultrasound pulses. By sequencing the firing, interference between the probes can be minimized.

The master can program the triggering sequence of the slaves as required by application logic. Once the triggering sequence is determined, the probes can be triggered to fire their ultrasound pulses either by the master they are paired to or else by a prior probe in the sequence.

The triggering can alternatively be timed-based using a global clock synchronization mechanism. In this method the system has a global clock with which all the slaves are synchronized. During a period of probe initialization, the slaves synchronize local clocks with the global clock. Further, depending on the sampling frequency of the probes in the sequence, the master can assign an absolute time to trigger the probes to fire repeatedly in their sequence.

Image acquisition using multiple probes will now be described in greater detail. In the case of a single probe, the transmitted and received ultrasound signal co-ordination happens within the probe. In the multi-probe (or dual probe) scenario of the invention, signal co-ordination needs to happen at inter-probe level. At inter-probe level, the ultrasound waves must be transmitted and received without any overlap of signals between the probes. In the absence of probe co-ordination, the captured images from different probes may contain echo interferences. This is caused by the overlapping of signals from the other probes—as illustrated in FIG. 1 by the signal 7a being received by probe 2a as echo signal 7b from probe 2b, and the signal 7c being received by probe 2b as echo signal 7d from probe 2c.

Ultrasonic signal co-ordination across probes is achieved either by an asynchronous or stateless protocol or by a synchronous protocol.

The image data acquired from the probes by the control unit may be processed either in the control unit itself or in external apparatus (not shown). The image data are rendered for display, so that the images are combined and are viewable together, the display of the images being simultaneous or substantially simultaneous such that the viewer can view them all together.

Figure 2:
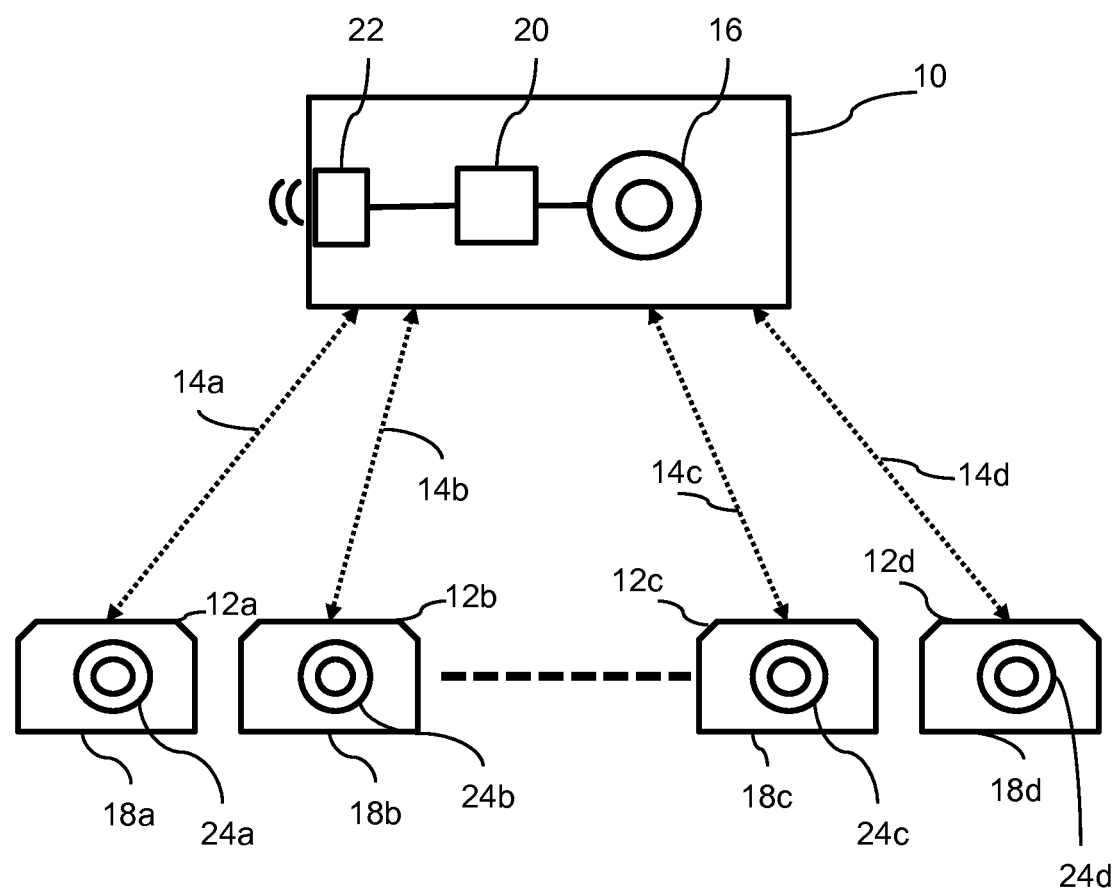
FIG. 2 shows a first system embodying the invention.

In the first embodiment described with reference to FIG. 2, a master control unit 10 communicates with slave probes 12a, 12b, 12c and 12d, and optionally additional similar probes (not shown), over paths represented by lines 14a, 14b, 14c and 14d. A global clock 16 in the control unit 10 is provided, and this may be set by an external global clock (not shown), for example by a server over the Internet, or by a relay message from another control unit. Internal local clocks 18a, 18b, 18c and 18d in the respective connected probes are synchronized from the global clock over the same paths of communication 14a-14d.

The control unit comprises a data processor 20 running an application which controls the whole system of master and slaves, and which communicates through a communications unit 22 with the probes and with external networks such as other control units, hospital systems and the Internet. The control unit 10 sends beamforming control commands to the probes. It also communicates to each probe the start time for the probe scan and the duration of the scan, which are specifically calculated based on the individual probe's parameters and the predetermined sequential order of probes in the scanning sequence. The probe parameters are preferably transmitted, upon request, to the control unit 10 during the initialization process which is run by the application in the data processor 20. These parameters, preferably including an address such as an IP address for the probe, are stored by the data processor 20.

The probe-specific timing information helps each individual probe to know when to start and stop its beamforming sequence of transmission and echo reception, without overlapping with other probe signals.

An advantage of this asynchronous, stateless probe co-ordination method is that it allows each individual probe to operate, once initially triggered, without depending on or communicating further either with the master or with the other probes involved in the beamforming sequence, except to transmit the echo data for the image to the control unit 10. Communications are minimized in this way. Also, each probe firing sequence can be repeated, under the control of the application running in the master control unit 10, for as long as the probes are reliably operating according to the global time. Periodic synchronization of the local clocks is executed—the frequency of this may depend on the accuracy of the local clocks which can be one of their parameters known to the control unit.

Figure 3:
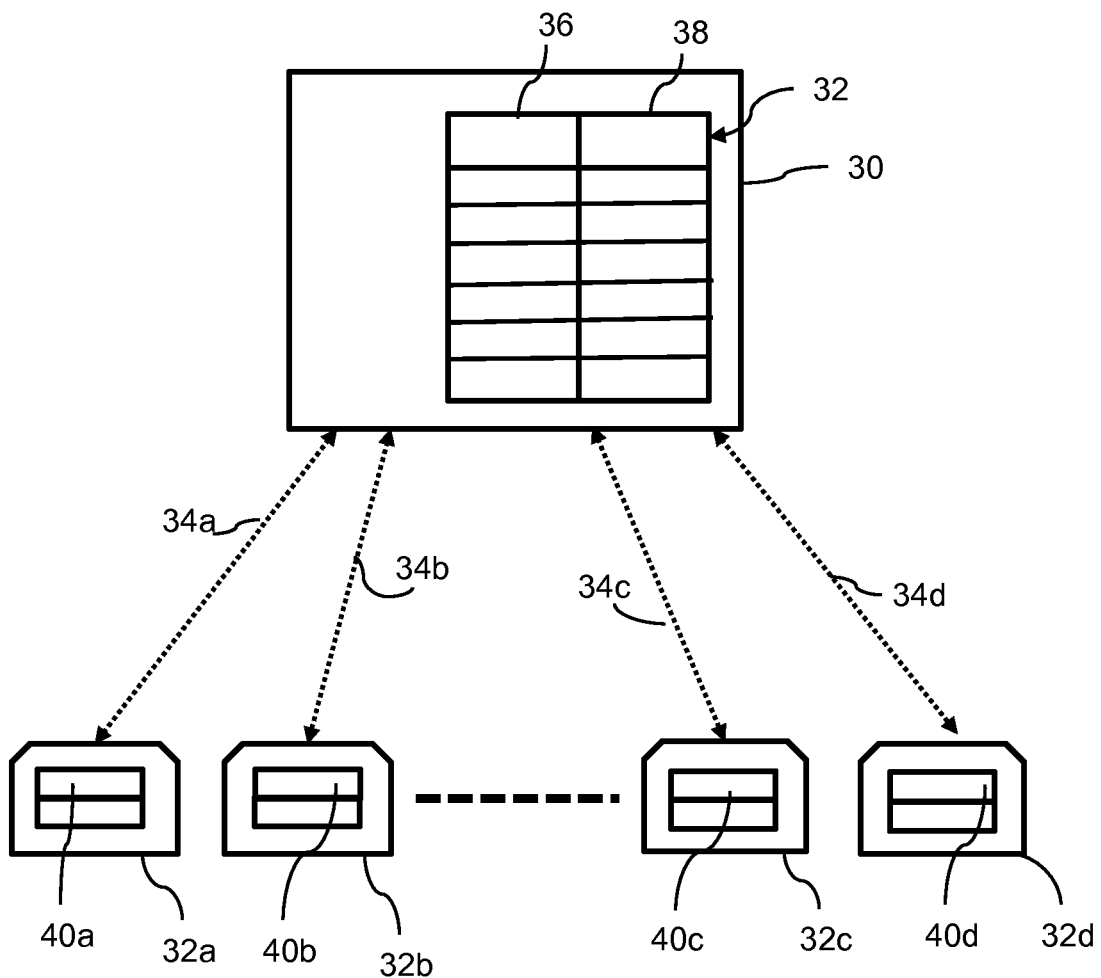
FIG. 3 shows a second system embodying the invention.

A second embodiment will now be described with reference to FIG. 3, which shows a synchronous, stateful system in which co-ordination between probes is done by tracking the state of the probes involved. Probe state communication is achieved in this embodiment by the control unit 30 acting as master to the probes 32a, 32b, 32c and 32d (and optionally additional probes not shown). As with the first embodiment, each probe communicates with the control unit 30 as represented by lines 34a, 34b, 34c and 34d.

The application in the data processor of the control unit 30 stores a register 32 of the states of all the slave probes, whose unique identities form one part 36 of the register, shown as the left-hand column in the drawing. The register stores the scan state of each identified probe, and this is represented as column 38 in the drawing. The scan state may be "Not started", "In progress" or "Completed"—although other states may be used, such as states indicative of a malfunction of the probe. Each probe also has a memory with a register 40a, 40b, 40c, 40d of its scan state. The probes send signals indicative of their scan states to the control unit 30. The application in the control unit continually updates the register 32 based on the updated scan states of the probes. It sends command signals to each probe in the predetermined probe sequence stored in the register 32, to cause that probe to start its scan sequence, which is the transmission and reception sequence, without interference from signals from other probes. This probe sequence may be repeated as many times as required.

Figure 4:
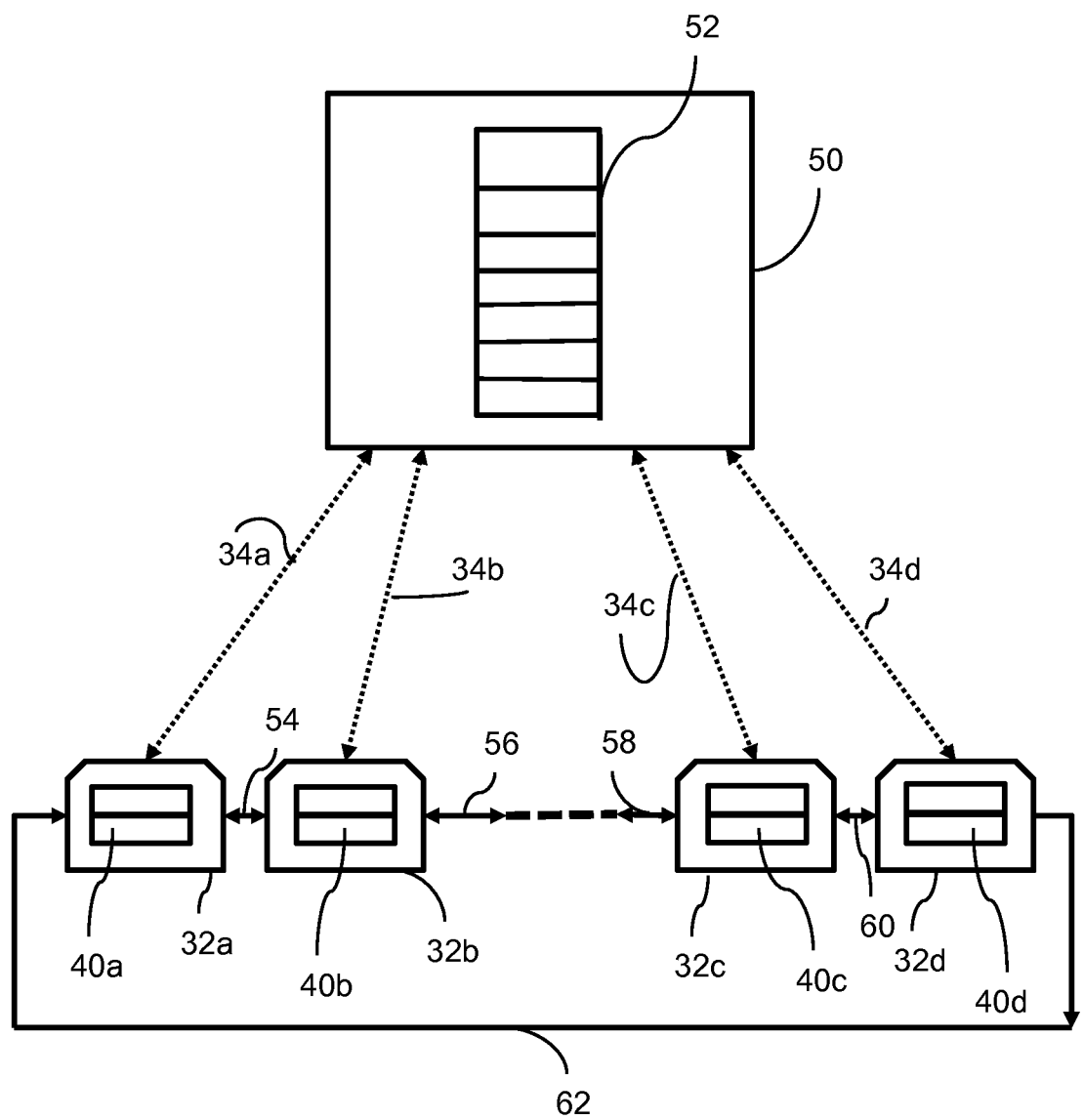
FIG. 4 shows a third system embodying the invention.

A third embodiment will now be described with reference to FIG. 4. This system is similar to that of FIG. 3, except that inter-probe communications are used for sequencing the probes. A register 52 in the master control unit 50 stores the triggering sequence of the connected probes 32a-32d. Each probe stores its own scan state, and also the identity of the probe that is the next in the firing sequence. Thus each probe can communicate with at least one other probe, and in most cases two other probes, and their communication paths are shown as 54, 56, 58, 60 and 62 in the drawing. As with the other embodiments, any number of probes may be used in the sequence. Beamforming begins with the first probe in the probe sequence set by the control unit 50 as master. The control unit 1 sends a command to the first probe 40a to initiate its scan, and also a signal indicative of the next probe, probe 32b, in the sequence. Instead of the identity of the probe, the signal could contain the IP address or some other means for the probe 32a to label or address its transmission on path 54 so that it is received and acted upon only by that next probe, probe 32b. On completion of its own scan sequence, the first probe 32a communicates its state with the next probe 32b, which is taken as an instruction for that next probe to start its own scan. The next, third probe 32c executes its scan when it is informed by the second probe 32b that its scan has completed. Finally, the fourth probe 32d executes its scan, and then its scan state is transmitted either to the control unit 50 or to the first probe 32a over path 62 for repeating the probe sequence.

The signals sent from probe to probe may include a counter indicative of the number of probe sequences that remain to be executed in the repeated sequential pattern of scans. The last probe 32d may then execute logic to select whether to send its scan state to the control unit 50 or to the first probe 32a, depending on whether the overall sequence is to be repeated.

There are scenarios where one of the probes captures a better view of the ROI than others. This may be because of their positions or the angles at which they are imaging the ROI. In all examples above, the application in the control unit 1, 10, 30, 50 may be adapted to respond to feedback data representing the quality of the ROI captured by each probe to prioritize the probes. For example, the application may dynamically change the sequential order of the triggering of the probes according to the calculated priority. Also, one or more of the probes may be temporarily eliminated from the sequence.

The formation of an image frame of the ROI comprising multiple lines may be obtained by beamforming and timing in the probe to select each scan line in sequence. For example, for each scan executed by a probe, the probe may acquire one image line and transmit that as image data to the control unit for temporary storage in relation to that probe. In the next cycle, i.e. when the probe sequence is repeated, the probe may then acquire the next image line and transmit it to the control unit. This may be repeated until a whole frame of a B-mode image has been acquired and stored for each probe in the control unit. The control unit may then display the image frames as soon as they have been generated. Alternatively, each probe could store each successive line in its own memory, and transmit a complete image frame to the control unit.

Thus, the scan sequence may build up the images line-by-line in an interleaved sequence, or else the complete image may be taken by one probe before the sequence moves to the next probe.

Figure 5:
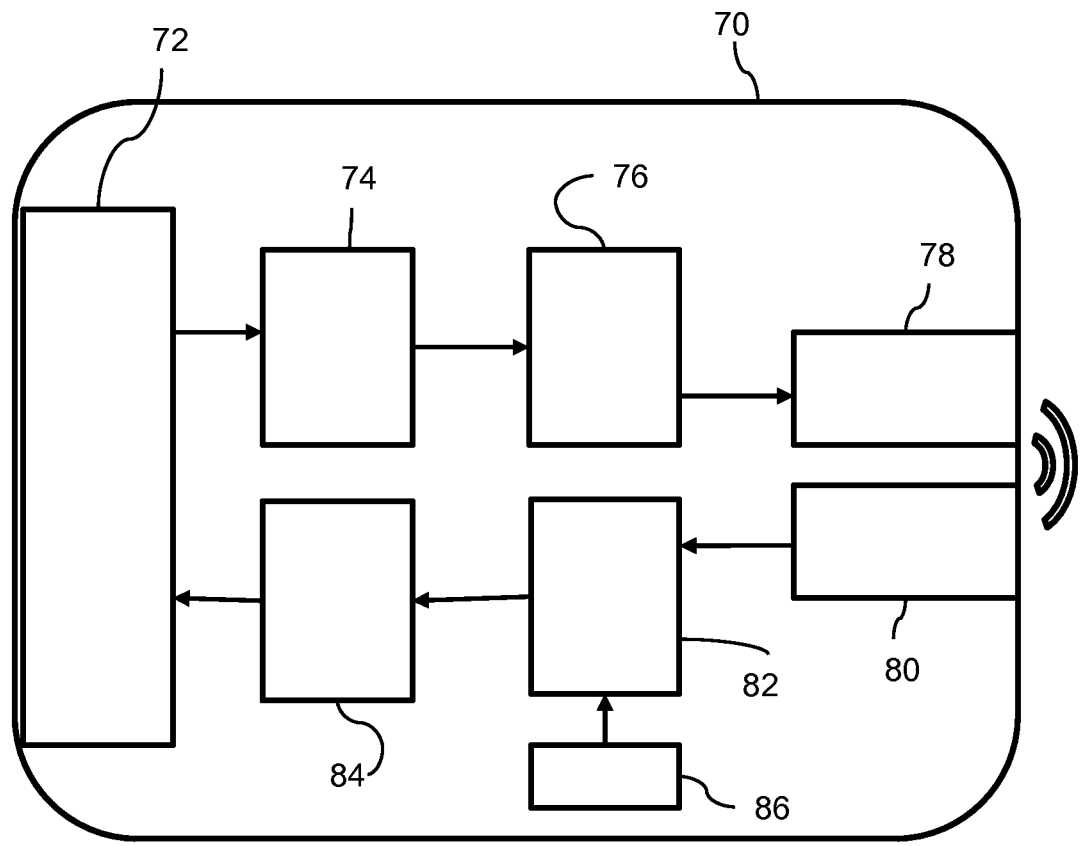
FIG. 5 shows an ultrasound probe for use in the systems of FIGS. 2 to 4.

An ultrasound probe 70 for use with any of the systems of FIGS. 1 to 4 is shown in FIG. 5. A piezoelectric transducer 72 having a fixed array of elements communicates with a sound-to-image converter 74 which sends an image signal to an image processing unit 76 for generating an image of the ROI. As described above, this may be a scan line obtained by scanning at a predetermined depth, and successive lines may be processed in the image processing unit 76, which may immediately send the image data to a transmission unit 78 for transmission to the control unit, or may accumulate multiple scan lines and then cause them to be transmitted together as a frame. The transmission unit 78 may also send control and other data signals to the other probes or to the control unit.

A receiver 80 is configured to receive signals from the control unit or the other probes, and to send signals to a multiplex controller 82, which coordinates the probes. The multiplex controller 82 receives and executes the probe co-ordination commands; activates and deactivates the piezoelectric sensor array 72 based on received triggering commands; communicates the probe scan state with the master control unit or another probe (in the case of the synchronous protocols of FIG. 3 or FIG. 4); and/or receives and synchronizes its local clock with the global clock (in the case of the synchronous, stateless protocol of FIG. 2).

Since the system involves using multiple probes for diagnosis, the preferred way for communicating data is, but is not restricted to, wireless communication channels such as a LAN which may be Wifi (Registered Trade Mark), short range RF such as Bluetooth (Registered Trade Mark); data may be transferred using any appropriate communication protocols. The probes could wirelessly communicate the captured images with the control unit in real time through an encrypted channel (via SSL, TLS, etc.). The receiving system could then decrypt the data and render it as a display to the user.

For each wireless probe to operate it should be continuously powered. The probe may have an internal battery, preferably rechargeable e.g. by contactless (wireless) charging. The probe 70 may also have a position sensor 86 such as a gyro sensor, accelerometer etc. and this may be used to localize each probe separately and to steer a power beam individually to each active probe, which can harvest the power from that beam. EP3181053A discloses a wireless ultrasound probe and a method of charging a battery included in the wireless ultrasound probe by receiving wireless power that is directionally transmitted toward the position of the wireless ultrasound probe and focusing received wireless power.

The localization information about each probe can also be used to focus the transmitted and/or received beam individually for each active probe. The control unit may determine the location and orientation of each probe from which it may determine their relative positions and/or their positions relative to the ROI, which may be used to process the images optimally for display.

Probe docking stations are preferably provided for recharging so that the probes may be used even during a power interruption. The docking station is preferably equipped with wireless charging capability.

Using multiple probes enables the user to view the ROI from different perspectives, thus giving a better insight for the diagnosis of the patient. Two or more perspectives of the same ROI may be generated by the two or more probes, which can be used for image stitching or blending i.e. fusing, to generate a single large field of view or a final image with better quality.

In addition, the multiple images from the probes can be used to generate 3D or higher dimensional sets of image data representing the volume of the organ of interest.

Different known rendering methods may be used, depending upon on the image acquisition method. The images captured from two or more probes may be displayed together or adjacent one another.

Figure 6:
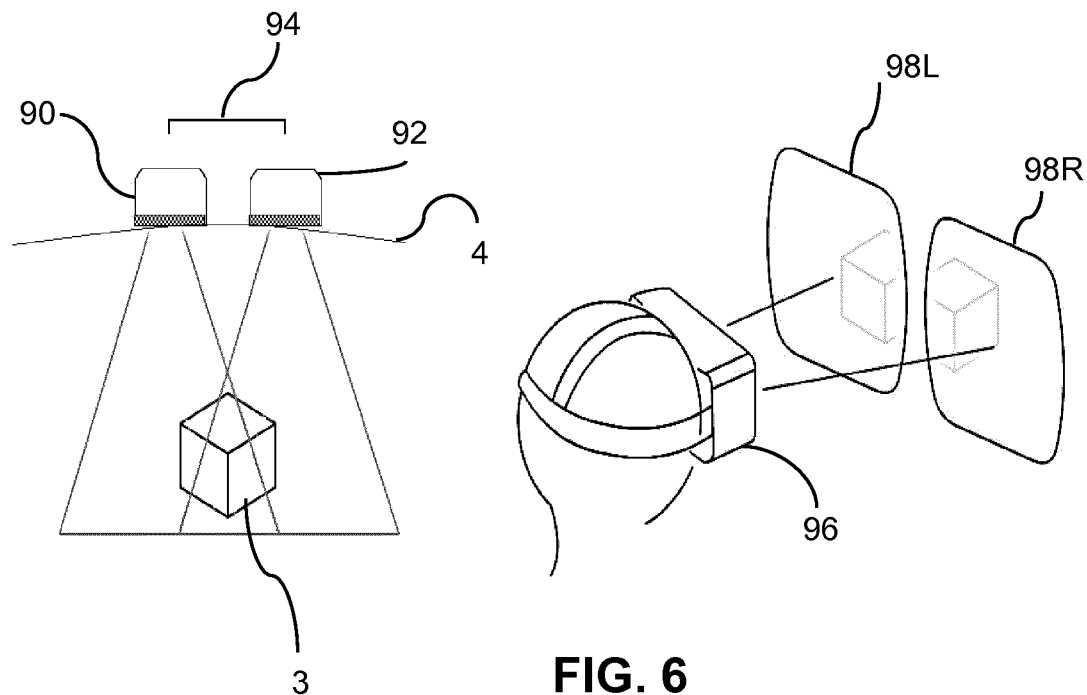
FIG. 6 shows stereoscopic ultrasound image display using the system of any of FIGS. 2 to 4.

Alternatively, a stereoscopic view using head mounted displays could be provided, as illustrated in FIG. 6. A region of interest 3 in the patient 4 is imaged using a pair of adjacent probes 90, 92 separated by the inter-pupillary distance 94 of the user, who wears a headset 96. Stereoscopic imaging is obtained by projecting the two images from the probes simultaneously or in quick succession as left eye 98L and right eye 98R images within the headset 96. This view gives depth perception.

As discussed above, embodiments make use of a control unit. The control unit can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Although the control unit is separate from the probes in the embodiments described, its functionality could instead be integrated into one or more of the probes.

The communications between the probes and the control unit are described as wireless in the embodiments, but they could be wired, by having cables between the probes or between the probes and the control unit, or both. In this case, the probes could be powered from an external source such as the control unit, and need not then have internal power sources. However, wired connections could make the usage of the probes more difficult and painful.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

The ultrasound probe has not been described in detail above, since the operation of an ultrasound imaging system is entirely conventional.

Figure 7:
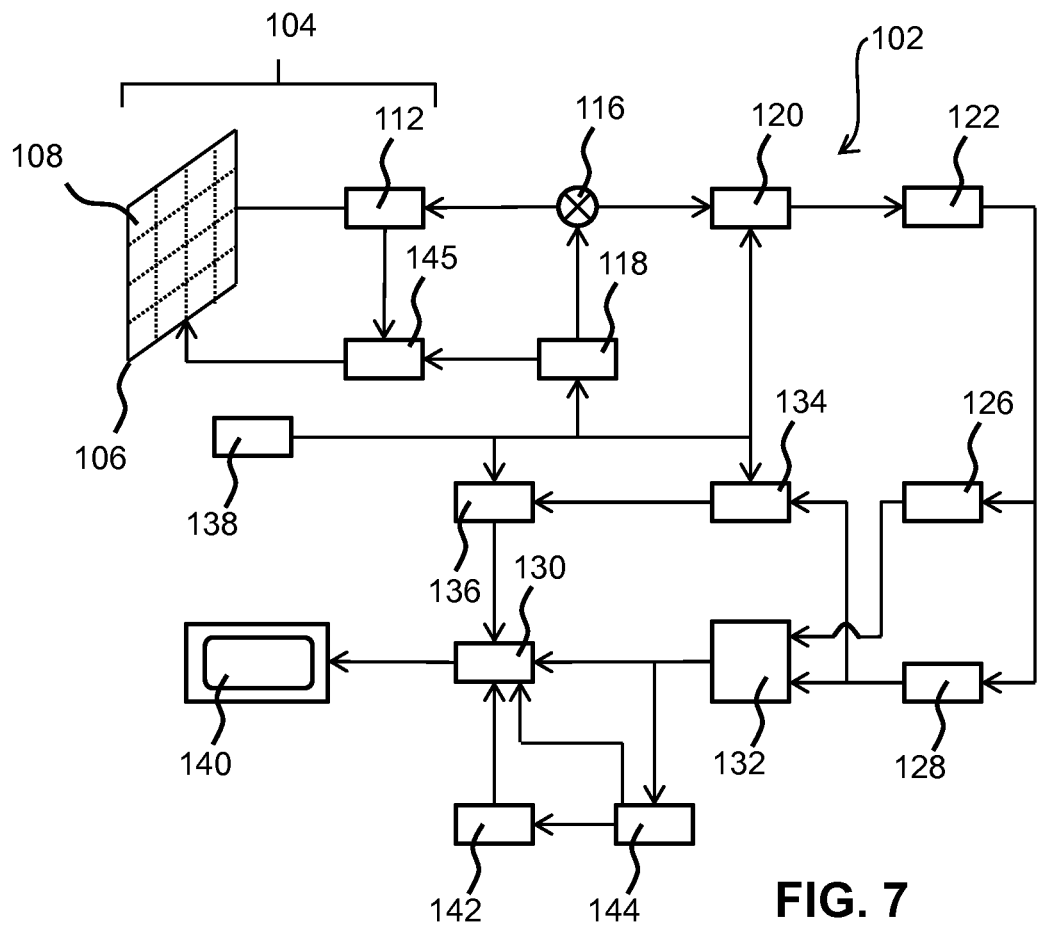
FIG. 7 shows an ultrasonic diagnostic imaging system with an array transducer probe in block diagram form.

For completeness, FIG. 7 shows an ultrasonic diagnostic imaging system 102 with an array transducer probe 104 in block diagram form.

The array transducer probe 104 comprises transducer cells. Traditionally, piezoelectric materials have been used for ultrasonic transducers. Examples are lead zirconate titanate (PZT) and polyvinylidene difluoride (PVDF) materials, with PZT being particularly popular as the material of choice. Single crystal piezoelectric materials are used to achieve high piezoelectric and electro-mechanical coupling constants for high performance transducers.

Recent developments have led to the prospect that medical ultrasound transducers can be batch manufactured by semiconductor processes. Desirably these processes should be the same ones used to produce the application specific integrated circuits (ASICs) needed by an ultrasound probe such as a CMOS process, particularly for 3D ultrasound. These developments have produced micro machined ultrasonic transducers or MUTs, the preferred form being the capacitive MUT (CMUT). CMUT transducers are tiny diaphragm-like devices with electrodes that convert the sound vibration of a received ultrasound signal into a modulated capacitance.

CMUT transducers in particular are able to function over a broad bandwidth, enable high resolution and high sensitivity imaging, and produce a large pressure output so that a large depth of field of acoustic signals can be received at ultrasonic frequencies. FIG. 7 shows a transducer array 106 of CMUT cells 108 as discussed above for transmitting ultrasonic waves and receiving echo information. The transducer array 106 of the system 102 may generally be a one- or a two-dimensional array of transducer elements capable of scanning in a 2D plane or in three dimensions for 3D imaging.

The transducer array 106 is coupled to a micro-beamformer 112 which controls transmission and reception of signals by the CMUT array cells. Micro-beamformers are capable of at least partial beamforming of the signals received by groups or "patches" of transducer elements for instance as described in U.S. Pat. No. 5,997,479 (Savord et al.), U.S. Pat. No. 6,013,032 (Savord), and U.S. Pat. No. 6,623,432 (Powers et al.)

The micro-beamformer 112 is coupled by the probe cable, e.g. coaxial wire, to a transmit/receive (T/R) switch 116 which switches between transmission and reception modes and protects the main beamformer 120 from high energy transmit signals when a micro-beamformer is not present or used and the transducer array 106 is operated directly by the main system beamformer 120. The transmission of ultrasonic beams from the transducer array 106 under control of the micro-beamformer 112 is directed by a transducer controller 118 coupled to the micro-beamformer by the T/R switch 116 and the main system beamformer 120, which receives input from the user's operation of the user interface or control panel 138. One of the functions controlled by the transducer controller 118 is the direction in which beams are steered and focused. Beams may be steered straight ahead from (orthogonal to) the transducer array 106, or at different angles for a wider field of view.

The transducer controller 118 may be coupled to control a voltage source 145 for the transducer array. For instance, the voltage source 145 sets DC and AC bias voltage(s) that are applied to the CMUT cells of a CMUT array 106, e.g. to generate the ultrasonic RF pulses in transmission mode.

The partially beam-formed signals produced by the micro-beamformer 112 are forwarded to the main beamformer 120 where partially beam-formed signals from individual patches of transducer elements are combined into a fully beam-formed signal. For example, the main beamformer 120 may have 128 channels, each of which receives a partially beam-formed signal from a patch of dozens or hundreds of CMUT transducer cells 108. In this way the signals received by thousands of transducer elements of a transducer array 106 can contribute efficiently to a single beam-formed signal.

The beam-formed signals are coupled to a signal processor 122. The signal processor 122 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles.

The signal processor 122 optionally may perform additional signal enhancement such as speckle reduction, signal compounding, and noise elimination. The bandpass filter in the signal processor 122 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B-mode processor 126 and optionally to a Doppler processor 128. The B-mode processor 126 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 128, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B-mode (and Doppler) processor(s) are coupled to a scan converter 132 and a multiplanar reformatter 144. The scan converter 132 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 144 will convert echoes which are received from points in a common plane in a volumetric region of the body into an ultrasonic image of that plane, for instance as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.)

The 2D or 3D images are coupled from the scan converter 132, multiplanar reformatter 144, and volume renderer 142 to an image processor 130 for further enhancement, buffering and temporary storage for display on an image display 140. In addition to being used for imaging, the blood flow values produced by the Doppler processor 128 and tissue structure information produced by the B-mode processor 126 are coupled to a quantification processor 134. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 136 for the reproduction of measurement graphics and values with the image on the display 140. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 138, such as patient name.

The user interface is also coupled to the transmit controller 118 to control the generation of ultrasound signals from the transducer array 106 and hence the images produced by the transducer array and the ultrasound system. The user interface is also coupled to the multiplanar reformatter 144 for selection and control of the planes of multiple multiplanar reformatted (MPR) images which may be used to perform quantified measures in the image field of the MPR images.

As will be understood by the skilled person, the above embodiment of an ultrasonic diagnostic imaging system is intended to give a non-limiting example of such an ultrasonic diagnostic imaging system. The skilled person will immediately realize that several variations in the architecture of the ultrasonic diagnostic imaging system are feasible without departing from the teachings of the present invention. For instance, as also indicated in the above embodiment, the micro-beamformer 112 and/or the Doppler processor 128 may be omitted, the ultrasound probe 104 may not have 3D imaging capabilities and so on.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. An ultrasound imaging apparatus for imaging a region of interest in a subject, the apparatus comprising:
    a control unit; and
    a plurality of ultrasonic probes coupled to the control unit and configured to perform ultrasound scans of the region of interest from different angles, each ultrasonic probe comprising:
        at least one transducer for transmitting and receiving ultrasonic waves;
        a receiver for receiving a probe scan signal for triggering an ultrasound scan of the region of interest by the ultrasonic probe; and
        an output for providing an ultrasound image;
    wherein the control unit is configured to:
        control the plurality of ultrasonic probes to coordinate respective operations in a predetermined probe sequence; and
        receive ultrasonic images from the outputs of the plurality of ultrasonic probes, for generating a combined display of the ultrasonic images from the plurality of ultrasonic probes; and
    wherein the operations of the plurality of ultrasonic probes are coordinated in the predetermined probe sequence by each ultrasonic probe transmitting a scan state signal indicative of the ultrasound scan being completed, for reception by a next ultrasonic probe in the predetermined probe sequence as the probe scan signal for the next ultrasonic probe, or for reception by the control unit for sending the probe scan signal to the next ultrasonic probe in the predetermined probe sequence.

2. The apparatus according to claim 1, wherein each probe comprises a memory configured to store a scan state representing a stage of progress of the ultrasound scan, the control unit being configured to transmit control signals to the ultrasonic probes to control the ultrasonic probes to switch sequentially between the scan states, whereby only one of the ultrasonic probes, which is the next in the predetermined probe sequence, commences the ultrasound scan in response to information, contained in the control signal it receives, that the scan state of another ultrasonic probe, a current ultrasonic probe in the predetermined probe sequence, represents completion of its ultrasound scan.

3. The apparatus according to claim 2, wherein a memory of the control unit is configured to store the scan state representing a stage of progress of the scan of each ultrasonic probe, and the control unit is configured to transmit and receive the control signals to and from each ultrasonic probe, to instruct a first probe of the plurality of ultrasonic probes in the predetermined probe sequence to start its scan and then to instruct each next ultrasonic probe in the predetermined probe sequence to start its scan only once it has received from a previous ultrasonic probe in the predetermined probe sequence the information that it has completed its scan.

4. The apparatus according to claim 3, wherein the memory of the control unit is configured to store the predetermined probe sequence, and to transmit a control signal to the first probe in the predetermined probe sequence to instruct it to start its scan;
    and each ultrasonic probe is configured, when it has completed its scan, to transmit a control signal to another of the plurality of ultrasonic probes, which is the next in the predetermined probe sequence, to instruct that other ultrasonic probe to start its scan.

5. The apparatus according to claim 1, wherein the control unit is configured to store probe position data representing a position of each ultrasonic probe, and to combine image data based on relative positions of the plurality of ultrasonic probes.

6. The apparatus according to claim 5, wherein each ultrasonic probe is configured to track its position and to store corresponding position data in a memory.

7. The apparatus according to claim 1, wherein each ultrasonic probe comprises an internal electric power source and a communications unit configured for wireless communication with the control unit and/or the other ultrasonic probes.

8. The apparatus according to claim 1, wherein the control unit is configured to combine the ultrasound images sequentially obtained from two of the ultrasonic probes that are separated by an inter-pupillary distance, to generate the combined display as a stereoscopic display for left eye and right eye projections.

9. A method of ultrasound imaging a region of interest in a subject, using a plurality of ultrasonic probes disposed at different positions on a subject to view the region of interest, the plurality of ultrasonic probes being coupled to a control unit, each ultrasonic probe comprising a receiver for receiving a probe scan signal for triggering an ultrasound scan by the ultrasonic probe, the method comprising:
    causing the ultrasonic probes to sequentially execute respective ultrasound scans in a predetermined probe sequence in response to probe scan signals, each ultrasonic scan comprising transmitting an ultrasonic beam to the region of interest and receiving reflections; and
    combining image data from the ultrasonic probes for simultaneous display;
    wherein the ultrasonic probes sequentially execute the respective ultrasound scans in the predetermined probe sequence by each ultrasonic probe transmitting a scan state signal indicative of its own ultrasound scan being completed, for reception by a next ultrasound probe as the probe scan signal, or for reception by the control unit for sending the next ultrasound probe the probe scan signal.

10. The method according to claim 9, wherein each ultrasonic probe stores a scan state representing a stage of progress of its own ultrasound scan, each ultrasonic probe executing its respective ultrasound scan by switching between scan states, whereby only one of the ultrasonic probes, which is next in the predetermined probe sequence, commences the ultrasound scan in response to information that a current ultrasonic probe in the predetermined probe sequence has completed its ultrasound scan.

11. The method according to claim 10, further comprising:
storing centrally a scan state representing the stage of progress of the ultrasound scan of each ultrasonic probe, and using the stored scan state to instruct a first ultrasonic probe of the plurality of ultrasonic probes in the predetermined probe sequence to start its ultrasound scan and then to instruct each next ultrasonic probe in the predetermined probe sequence to start its ultrasound scan only once a previous ultrasonic probe in the predetermined probe sequence has completed its ultrasound scan; or
instructing the first ultrasonic probe of the plurality of ultrasonic probes in the predetermined probe sequence to start its ultrasound scan, when each ultrasound probe has completed its ultrasound scan, instructing a next ultrasonic probe in the predetermined probe sequence to start its ultrasound scan.

12. The method according to claim 9, wherein each ultrasonic probe tracks its position, and wherein the image data are combined based on relative positions of the ultrasonic probes.

13. An ultrasound imaging apparatus for imaging a region of interest in a subject, the apparatus comprising:
a control unit comprising a global clock for generating a global clock signal; and
a plurality of ultrasonic probes coupled to the control unit and configured to perform ultrasound scans of the region of interest from different angles, each ultrasonic probe comprising:
at least one transducer for transmitting and receiving ultrasonic waves;
a receiver for receiving from the control unit the global clock signal and probe-specific information for initiating an ultrasound scan of the region of interest by the ultrasonic probe, the probe-specific information comprising a start time and a duration of the ultrasound scan;
a local clock synchronized with the global clock, which is common to the plurality of ultrasonic probes; and
an output for providing an ultrasound image;
wherein respective operations of the plurality of ultrasonic probes are coordinated in a predetermined probe sequence by each ultrasonic probe storing the local clock synchronized to the global clock and executing the ultrasound scan at a scan timing based on the probe-specific information to ensure sequential operation of the plurality of ultrasound probes so as to avoid mutual interference between the respective ultrasonic waves.

14. The apparatus according to claim 13, wherein the probe-specific information comprises a predetermined set of beamforming parameters for the transmitting and receiving of the ultrasonic waves in accordance with local time determined by the local clock;
wherein the control unit is configured periodically to set or reset the local clocks by transmitting the global clock signal to each respective ultrasonic probe; and
wherein the beamforming parameters comprise sequencing information including the predetermined probe sequence.

* * * * *